(12) United States Patent
Addison et al.

(10) Patent No.: US 12,178,602 B2
(45) Date of Patent: Dec. 31, 2024

(54) NOCICEPTION STIMULUS FEEDBACK CONTROL FOR DRUG TITRATION DURING SURGERY

(71) Applicant: Covidien LP, Mansfield, MA (US)

(72) Inventors: Paul S. Addison, Edinburgh (GB); Dean Montgomery, Edinburgh (GB)

(73) Assignee: COVIDIEN LP, Mansfield, MA (US)

( * ) Notice: Subject to any disclaimer, the term of this patent is extended or adjusted under 35 U.S.C. 154(b) by 1199 days.

(21) Appl. No.: 16/933,745

(22) Filed: Jul. 20, 2020

(65) Prior Publication Data

US 2022/0015696 A1 Jan. 20, 2022

(51) Int. Cl.
| | | |
|---|---|---|
| *A61B 5/00* | (2006.01) | |
| *A61B 5/1455* | (2006.01) | |
| *A61B 34/00* | (2016.01) | |
| *A61B 34/10* | (2016.01) | |
| *A61B 34/30* | (2016.01) | |
| *G16H 20/10* | (2018.01) | |
| *G16H 20/17* | (2018.01) | |
| *G16H 40/63* | (2018.01) | |
| *A61B 5/021* | (2006.01) | |

(52) U.S. Cl.
CPC ........ *A61B 5/4821* (2013.01); *A61B 5/14551* (2013.01); *A61B 5/7282* (2013.01); *A61B 34/10* (2016.02); *A61B 34/25* (2016.02); *A61B 34/30* (2016.02); *G16H 20/10* (2018.01); *G16H 20/17* (2018.01); *G16H 40/63* (2018.01); *A61B 5/021* (2013.01); *A61B 2505/05* (2013.01)

(58) Field of Classification Search
None
See application file for complete search history.

(56) References Cited

U.S. PATENT DOCUMENTS

| | | |
|---|---|---|
| 7,407,485 B2 | 8/2008 | Huiku |
| 7,407,486 B2 | 8/2008 | Huiku et al. |
| 8,463,370 B2 | 6/2013 | Korhonen et al. |
| 8,574,156 B2 | 11/2013 | Uutela et al. |

(Continued)

FOREIGN PATENT DOCUMENTS

| | | |
|---|---|---|
| CN | 108376559 A | 8/2018 |
| JP | 2010081950 A | 4/2010 |

(Continued)

OTHER PUBLICATIONS

Chanques et al., "Analgesia nociception index for the assessment of pain in critically ill patients: a diagnostic accuracy study," British Journal of Anaesthesia, vol. 119, No. 4, Elsevier Ltd., Oct. 2017, pp. 812-820.

(Continued)

*Primary Examiner* — Manuel A Mendez
(74) *Attorney, Agent, or Firm* — Fletcher Yoder, P.C.

(57) ABSTRACT

A patient monitoring system may include processing circuitry configured to receive an indication of a surgical event, obtain a nociception parameter of a patient, compare the nociception parameter of the patient to a nociception threshold to detect a nociception event, determine whether the surgical event corresponds to the nociception event, and in response to determinizing whether the surgical event corresponds to the nociception event, provide an indication to adjust an amount of analgesic administered to the patient.

20 Claims, 7 Drawing Sheets

(56) References Cited

U.S. PATENT DOCUMENTS

| | | | |
|---|---|---|---|
| 8,641,632 | B2 | 2/2014 | Quintin et al. |
| 8,862,238 | B2 | 10/2014 | Rahimi et al. |
| 9,326,725 | B2 | 5/2016 | Finkel et al. |
| 9,402,558 | B2 | 8/2016 | John et al. |
| 9,579,457 | B2 | 2/2017 | Osorio et al. |
| 9,861,317 | B2 | 1/2018 | Ochs |
| 10,285,597 | B2 | 5/2019 | Franz et al. |
| 10,388,405 | B2 | 8/2019 | Verghese |
| 2008/0242955 | A1 | 10/2008 | Uutela et al. |
| 2008/0319274 | A1 | 12/2008 | Ballegaard et al. |
| 2011/0082440 | A1 | 4/2011 | Kimmo et al. |
| 2011/0118619 | A1 | 5/2011 | Burton et al. |
| 2012/0226186 | A1 | 9/2012 | Baars et al. |
| 2013/0150748 | A1 | 6/2013 | Jensen |
| 2014/0194859 | A1* | 7/2014 | Ianchulev ........... A61F 9/00825 606/6 |
| 2014/0276549 | A1 | 9/2014 | Osorio |
| 2015/0201879 | A1 | 7/2015 | Hargrove |
| 2016/0331248 | A1* | 11/2016 | Satish .................... G16H 40/63 |
| 2018/0000409 | A1 | 1/2018 | Jensen et al. |
| 2018/0085055 | A1 | 3/2018 | Annoni et al. |
| 2018/0206784 | A1 | 7/2018 | Jensen et al. |
| 2018/0310877 | A1* | 11/2018 | Zuckerman Stark .. A61B 5/392 |

FOREIGN PATENT DOCUMENTS

| | | | |
|---|---|---|---|
| WO | 2009063463 | A2 | 5/2009 |
| WO | 2013140106 | A1 | 9/2013 |
| WO | 2018019214 | A1 | 2/2018 |
| WO | 2019211335 | A1 | 11/2019 |

OTHER PUBLICATIONS

International Preliminary Report on Patentability from International Application No. PCT/US2021/042221 dated Feb. 2, 2023, 8 pp.
Julien-Marsollier et al., "Evaluation of the analgesia nociception index for monitoring intraoperative analgesia in children", British Journal of Anaesthesia, vol. 121, No. 2, Elsevier, Apr. 26, 2018, pp. 462-468, doi: 10.1016/j.bja.2018.03.034.
U.S. Appl. No. 18/249,524, filed Nov. 17, 2021, naming inventors Addison et al.
U.S. Appl. No. 18/249,945, filed Nov. 18, 2021, naming inventors Addison et al.
Funcke et al., "Guiding Opioid Administration by 3 Different Analgesia Nociception Monitoring Indices During General Anesthesia Alters Intraoperative Sufentanil Consumption and Stress Hormone Release: A Randomized Controlled Pilot Study", Anesthesia & Analgesia, May 20, 2020, pp. 1-9.
Hemmerling et al., "Robotic Anesthesia—A Vision for the Future of Anesthesia", Departments of Anesthesia, McGill University, Sep.-Dec. 2011, pp. 1-20.
Medasense Pain Intelligence, www.medasense.com, 2017, 34 pp.(Applicant points out, in accordance with MPEP 609.04(a), that the year of publication, 2017, is sufficiently earlier than the effective U.S. filing date, so that the particular month of publication is not in issue.).
International Search Report and Written Opinion of International Application No. PCT/US2021/042221, mailed Nov. 3, 2021, 15 pp.

* cited by examiner

NOCICEPTION STIMULUS FEEDBACK CONTROL FOR DRUG TITRATION DURING SURGERY

TECHNICAL FIELD

This disclosure relates to patient monitoring.

BACKGROUND

Nociception is a response of a sensory nervous system of a subject to certain stimuli, such as chemical, mechanical, or thermal stimuli, that causes the stimulation of sensory nerve cells called nociceptors.

SUMMARY

The present disclosure describes example devices, systems, and techniques for monitoring the nociception parameters of a patient undergoing robot-assisted surgery to help determine the amount of analgesic to administer to the patient during the surgery. A clinician may use a nociception monitoring system to monitor the nociception parameters of the patient during surgery. As the patient undergoes the surgery, the clinician may administer analgesic to the patient to reduce the surgical stress experienced by the patient during surgery.

The nociception parameters of the patient may correspond to the amount of surgical stress caused to the patient. When the nociception parameter of the patient increases to be greater than or equal to a nociception threshold, the nociception parameter may indicate a severe nociceptive stimulus. Correspondingly, the clinician may, in response to the nociception parameter indicating a severe nociceptive stimulus, increase the amount of analgesic being administered to the patient to dampen down the nociception response of the patient and hence reduce the surgical stress caused to the patient.

In some examples, a method includes receiving, by processing circuitry, an indication of a surgical event, obtaining, by the processing circuitry, a nociception parameter of a patient, comparing, by the processing circuitry, the nociception parameter of the patient to a nociception threshold to detect a nociception event, determining, by the processing circuitry, whether the surgical event corresponds to the nociception event, and in response to determining whether the surgical event corresponds to the nociception event, providing, by the processing circuitry, an indication to adjust an amount of analgesic administered to the patient.

In some examples, a system includes memory configured to store a nociception threshold. The system further includes processing circuitry configured to: receive an indication of a surgical event; obtain a nociception parameter of a patient; compare the nociception parameter of the patient to the nociception threshold to detect a nociception event; determine whether the surgical event corresponds to the nociception event; and in response to determining whether the surgical event corresponds to the nociception event, provide an indication to adjust an amount of analgesic administered to the patient.

In some examples, a non-transitory computer readable storage medium comprises instructions that, when executed, cause processing circuitry to: receive an indication of a surgical event; obtain a nociception parameter of a patient; compare the nociception parameter of the patient to a nociception threshold to detect a nociception event; determine whether the surgical event corresponds to the nociception event; and in response to determinizing whether the surgical event corresponds to the nociception event, provide an indication to adjust an amount of analgesic to administer to the patient.

The details of one or more examples are set forth in the accompanying drawings and the description below. Other features, objects, and advantages will be apparent from the description and drawings, and from the claims.

DETAILED DESCRIPTION

Figure 1:
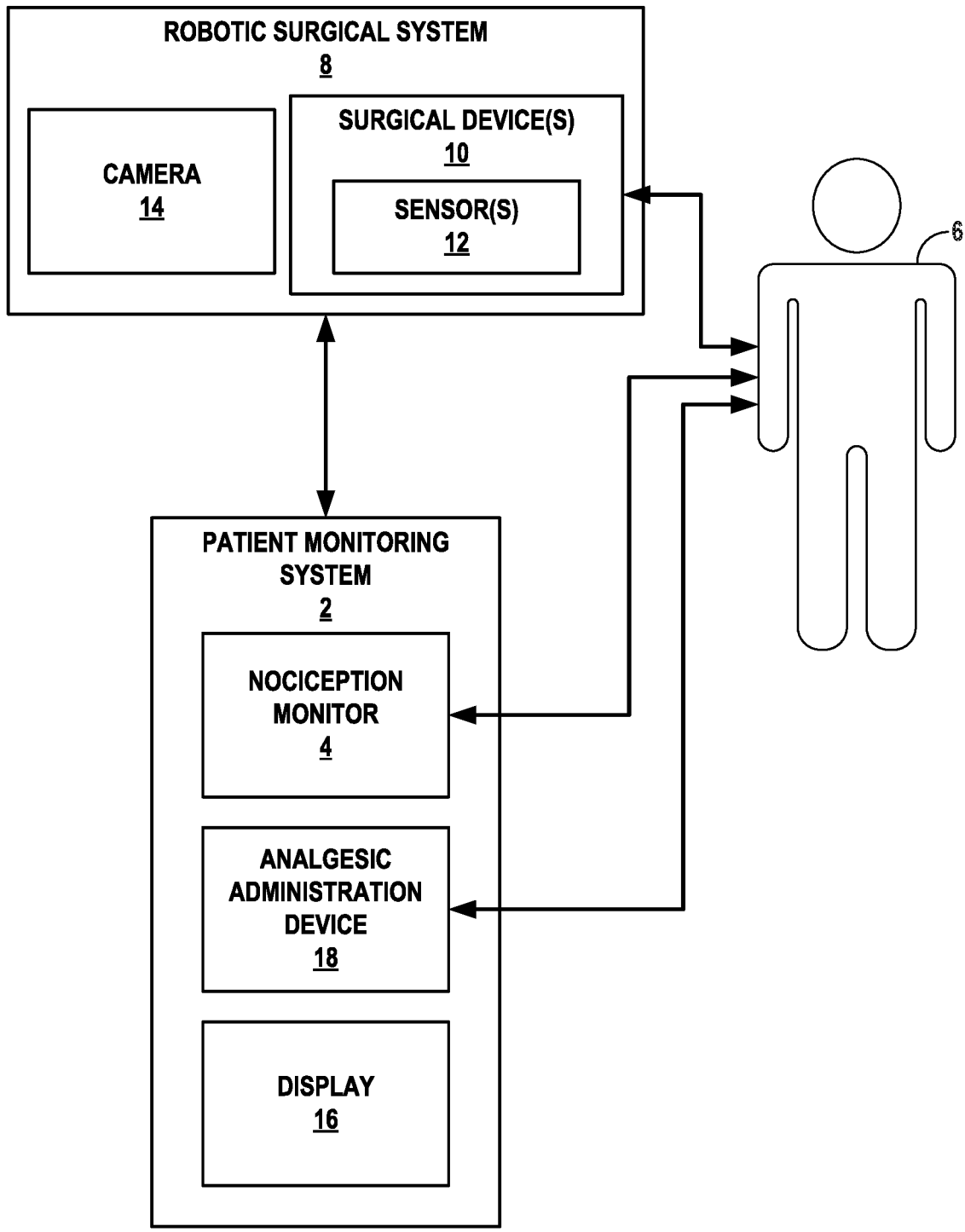
FIG. 1 is a block diagram illustrating an example environment in which a patient monitoring system monitors the nociception parameters of a patient undergoing robot-assisted surgery, in accordance with aspects of this disclosure.

Aspects of the present disclosure describe techniques for monitoring the nociception parameters of a patient undergoing robot-assisted surgery to help determine the amount of analgesic to administer to the patient during the surgery. A clinician may use a nociception monitoring system to monitor the nociception parameters of the patient during surgery. As the patient undergoes the surgery, the clinician may administer analgesic to the patient to reduce the surgical stress experienced by the patient during surgery.

Nociception monitors may provide a continuous measure of a nociception parameter for a patient undergoing surgery in order to track the nociception response of the patient. The nociception parameter can be based on one or more physiological signals, such as an electrocardiogram (ECG), a photoplethysmogram (PPG), electroencephalogram (EEG), skin conductance, body temperature, and the like, and may typically be displayed over time. A clinician may monitor the nociception parameter of a patient to determine the amount of analgesic to administer to the patient during surgery.

Noise in the nociception parameters may occasionally cause false positive indications of a severe nociceptive stimulus. Such noise may be caused by patient motion, electrocautery, administration of drugs to the patient, and the like, or may be present in underlying signals from which the nociception parameters are derived. For example, such noise may cause the nociception monitoring system to sense increases in the nociception parameters of the patient above the nociception threshold even when there is not a corresponding increase in the surgical stress experienced by the patient. If the clinician were to increase the amount of analgesic administered to the patient in response to such false positive indications of a severe nociceptive stimulus, the clinician may unwittingly administer additional analgesic to the patient where it may not be required. This disclosure describes devices, systems, and methods for reducing such false positives during surgery. In robotic surgery, a robotic surgical system may operate (e.g., make incisions) on a patient using surgical tools that are attached to the robotic surgical system. When a surgical tool makes an incision on a patient, the robotic surgical system may send an indication of the incision to a nociception monitoring system. Thus, when the nociception monitoring system determines that the nociception parameter of the patient is above the nociception threshold, the nociception monitoring system may determine, based on the indication of the incision received from the robotic surgical system, whether the nociception parameter being above the nociception threshold corresponds to the incision made by the robotic surgical system. If the nociception monitoring system determines that the nociception parameter being above the nociception threshold corresponds to the incision made by the robotic surgical system, then the nociception monitoring system may determine that the nociception parameter corresponds to an actual increase in the surgical stress experienced by the patient rather than being a false positive caused by, for example noise in the nociception parameters.

As such, by communicating with a robotic surgical system to receive indications of incisions made by the robotic surgical system, the devices, systems, and techniques of this disclosure may increase the accuracy of the nociception monitoring system in associating nociception parameters of a patient with real increases in the surgical stress experienced by the patient. Increasing the accuracy of the nociception monitoring system may lead to positive outcomes for the patient by at least enabling a clinician or an analgesic administration system to more accurately administer analgesic to the patient when it may be required to reduce the surgical stress caused to the patient and to decrease unnecessary administration of additional analgesic administered to the patient due to false positives.

FIG. 1 is a block diagram illustrating an example environment in which a patient monitoring system monitors one or more nociception parameters of a patient undergoing robot-assisted surgery. As shown in FIG. 1, a clinician (e.g., a surgeon) may use robotic surgical system 8 to perform surgery on patient 6. As the patient undergoes surgery, patient monitoring system 2 may monitor one or more physiological signals of patient 6 to determine the amount of surgical stress caused by the surgery to patient 6. By monitoring the amount of surgical stress experienced by patient 6, patient monitoring system 2 or a clinician that uses patient monitoring system 2 may be able to determine whether to increase amount of analgesic to administer to the patient during the surgery.

Robotic surgical system 8 may be a computerized system that includes hardware and software for assisting the clinician to perform surgery on patient 6. For example, robotic surgical system 8 may include one or more computer-controlled surgical instruments, and a clinician may interact with robotic surgical system 8 to control and move such surgical instruments in order to perform surgical procedures on patient 6. Example surgical instruments that can be controlled by control circuitry of robotic surgical system 8 include one or more surgical devices 10, such as scalpels, forceps, scissors, clamps, needles, retractors, suction tips, staplers, and the like. A clinician may interact with robotic surgical system 8 to control and move one or more surgical devices 10 in order to operate on patient 6, such as to make incisions in patient 6 and/or to perform surgical procedures through such incisions on patient 6. In some examples, one or more surgical devices 10 may include an endotracheal tube that may be intubated in patient 6 and extubated from patient 6.

In some examples, one or more sensors 12, such as accelerometers, force sensors, and the like may be coupled to one or more surgical devices 10, including being coupled to an endotracheal tube, to measure the amount of force exerted by one or more surgical devices 10 as one or more surgical devices 10 make incisions in patient 6. For example, a sensor can be mounted on the tip of one or more surgical devices 10 and generate a signal indicative of the force of one or more surgical devices 10 applies to make an incision in patient 6. In some examples, a sensor can also be mounted on, for example, an endotracheal tube of surgical devices 10 and may generate a signal indicative of the force of intubating the endotracheal tube in patient 6 or extubating the endotracheal tube from patient 6.

In some example, a signal generated by each sensor mounted on a surgical device of one or more surgical devices 10 may also identify the surgical device that the sensor is mounted to. Thus, processing circuitry of patient monitoring system 2 or another device may be able to identify the surgical device being used by robotic surgical system 8 based on an output generated by a sensor mounted to a surgical device. For example, a sensor may be able to identify the surgical device the sensor being mounted to as being a scalpel, an endotracheal tube, or other surgical device.

In some examples, robotic surgical system 8 may also include camera 14, such as a laparoscopic camera, an endoscopic camera, or any other surgical camera that may capture live images and/or live videos of the surgery site of patient 6 that a clinician controlling robotic surgical system 8 may view while performing surgery on patient 6.

Robotic surgical system 8 may be operably coupled with patient monitoring system via a wired or wireless network or via any other communications medium to communicate with patient monitoring system 2. Specifically, robotic surgical system 8 may communicate with patient monitoring system 2 to send indications of actions performed by one or more surgical devices 10 to operate on patient 6. For example, each time one or more surgical devices 10 makes an incision in patient 6, robotic surgical system 8 may send an indication of one or more surgical devices 10 making an incision in patient 6.

Patient monitoring system 2 is configured to monitor patient 6 during surgery and configured to titrate analgesic or anesthetic delivered to patient 6 during surgery to provide anesthesia for patient 6. Patient monitoring system 2 may include nociception monitor 4, analgesic administration device 18, and display 16. As the clinician performs surgery on patient 6 using robotic surgical system 8, nociception monitor 4 of patient monitoring system 2 may monitor the amount of surgical stress experienced by patient 6 by monitoring one or more physiological signals of patient 6, such as, but not limited to one or more of an ECG, a PPG, an EEG, the skin conductance of patient 6, the body temperature of patient 6, a respiratory rate, and the like, to determine a continuous measure of a nociception parameter associated with patient 6 during the surgery, where the nociception parameter corresponds to the amount of surgical stress experienced by patient 6. In some examples, the nociception parameter may be an integer, and may range from, for example, 0 to 100. As such, by determining a continuous measure of a nociception parameter associated with patient 6 during the surgery, nociception monitor 4 may determine a continuous measure of the amount of surgical stress experienced by patient 6 during surgery.

Display 16 is configured to display the nociception parameter over time. For example, as nociception monitor 4 determines the nociception parameter associated with patient 6, display 16 may output a graphical representation of the nociception parameter over time, which may be viewed by a clinician to monitor the amount of surgical stress experienced by patient 6.

In some examples, patient monitoring system 2 may include analgesic administration device 18, which may include one or more components and/or devices for administering analgesic to patient 6 during surgery. Analgesic administration device 18 may be coupled to patient 6, such as via one or more intravenous (IV) lines, a breathing mask, a tube, and the like, to titrate analgesic to patient 6 in order to provide anesthesia to patient 6 during surgery.

In some examples, the analgesic administration device 18 nay be able to administer analgesic to patient 6 without user intervention from, for example, a clinician. That is, patient monitoring system 2 may control the amount of analgesic being administered by analgesic administration device 18 to patient 6 (i.e., titrate analgesic delivered to patient 6), such as increasing the amount of analgesic administered by analgesic administration device 18 to patient 6 or decreasing the amount of analgesic administered by analgesic administration device 18 to patient 6, without user intervention.

In some examples, a clinician may control the amount of analgesic being administered by analgesic administration device 18 to patient 6. For example, the clinician may provide user input to patient monitoring system 2 indicative of the amount of analgesic being administered by analgesic administration device 18 to patient 6. Patient monitoring system 2 may receive such user input indicative of the amount of analgesic being administered by analgesic administration device 18 to patient 6 and may, in response, control analgesic administration device 18 to administer the amount of analgesic to patient 6 indicated by the user input.

As a medical procedure is performed on patient 6, such as by surgical system 8, nociception monitor 4 of patient monitoring system 2 may continuously determine the nociception parameter associated with patient 6 in order to monitor the amount of surgical stress experienced by patient 6. Nociception monitor 4 may specify a nociception threshold for patient 6, where nociception parameters of patient 6 that are at or above the nociception threshold may be indicative of patient 6 experiencing a severe nociceptive stimulus. In the example where the nociception parameter of patient 6 may range from 0 to 100, a nociception threshold may also be an integer value between 0 and 100, such as 70, 80, and the like. In some examples, the nociception parameter may be adjustable, such as by a clinician, so that the clinician may specify different nociception parameters for different patients or for different medical procedures performed on patient 6. As such, if nociception monitor 4 determines that the nociception parameter of patient 6 is greater than or equal to the nociception threshold, patient monitoring system 2 may detect that a nociception event has occurred and may accordingly increase the amount of analgesic administered by analgesic administration device 18 to patient 6 to dampen down the surgical stress experienced by patient 6 and to decrease the nociception parameter of patient 6 to below the nociception threshold.

However, noise in the nociception parameters may occasionally cause false positive indications of a severe nociceptive stimulus. For example, such noise may cause nociception monitor 4 to detect nociception events (e.g., increases in the nociception parameter of patient 6 to being greater than or equal to the nociception threshold) even when there is not a corresponding increase in the surgical stress experienced by patient 6. As such, instead of determining whether patient 6 is experiencing a severe nociceptive stimulus based only on the nociception parameter of patient 6, patient monitoring system 2 may communicate with robotic surgical system 8 to receive indications of surgical events, such as indications of incisions made in patient 6, and may use such indications of incisions made by robotic surgical system 8 along with the nociception parameter of patient 6 to determine whether patient 6 is actually experiencing a severe nociceptive stimulus.

In accordance with aspects of this disclosure, as robotic surgical system 8 performs a medical procedure on patient 6 using one or more surgical devices 10. For example, one or more surgical devices may make incisions in patient 6 or may intubate or extubate patient 6. Such actions such as making incisions in patient 6 or intubating or extubating patient 6 are herein referred to as surgical events.

Robotic surgical system 8 may, in response to making an incision in patient 6, intubating patient 6, or extubating patient 6, send an indication of a surgical event to patient monitoring system 2. For example, in response to making an incision on patient 6, robotic surgical system 8 may send, to patient monitoring system 2, an indication of a surgical event that is an indication of robotic surgical system 8 making the incision in patient 6. Similarly, in response to intubating or extubating patient 6, robotic surgical system 8 may send, to patient monitoring system 2, an indication of a surgical event that is an indication of robotic surgical system 8 intubating or extubating patient 6.

Patient monitoring system 2 may receive, from robotic surgical system 8, the indication of the surgical event, such as the indication of robotic surgical system 8 making the incision in patient 6 or the indication of robotic surgical system 8 intubating or extubating patient 6, and may use the indication of the surgical event in determining whether the nociception parameter of patient 6 exceeding the nociception threshold is a false positive, For example, processing circuitry of patient monitoring system 2 may obtain a nociception parameter of patient 6, such as by receiving the nociception parameter of patient 6 from nociception monitor 4. The processing circuitry of patient monitoring system 2 may detect a nociception event has occurred by comparing the nociception parameter of patient 6 to the nociception threshold for patient 6, such as by determining that a nociception parameter of patient 6 is greater than or equal to the nociception threshold 6. The processing circuitry of patient monitoring system 2 may determine, based at least in part on the indication of the surgical event, whether the occurrence of the nociception event corresponds to the surgical event. That is, patient monitoring system 2 may determine whether the surgical event corresponds in time to the occurrence of the surgical event (e.g., the nociception parameter of patient 6 being greater than or equal to the nociception threshold).

Patient monitoring system 2 may, in response to receiving the indication of the surgical event from robotic surgical system 8, set a surgical event flag, such as by setting the surgical event flag to a value indicative of the surgical event. If patient monitoring system 2 detects a nociception event while the surgical event flag is set, patient monitoring system 2 may determine that the nociception parameter of patient 6 is not a false positive and instead indicates patient 6 is actually experiencing a severe nociceptive stimulus. That is, if patient monitoring system 2 determines that the nociception event occurred while the surgical event flag is set, patient monitoring system 2 may determine that the surgical event corresponds in time to the nociception event. That is, the time at which the nociception event occurred corresponds to the time at which the surgical event occurred.

Patient monitoring system 2 may, in response to determinizing that the surgical event corresponds to the occurrence of the nociception event for patient 6, provide an indication to adjust an amount of analgesic to administer to patient 6. Thus, if patient monitoring system 2 determines that the nociception parameter of patient 6 is greater than or equal to the nociception threshold while the surgical event flag is set, patient monitoring system 2 may provide an indication to adjust an amount of analgesic to administer to patient 6, such as by providing an indication to increase the amount of analgesic to administer to patient 6.

In sonic examples, a clinician may manually control analgesic administration device 18 to administer analgesic to patient 6. As such, in order to provide an indication to adjust an amount of analgesic to administer to patient 6, patient monitoring system 2 may output, for display at display 16, an indication to a clinician to adjust the amount of analgesic administered to patient 6. For example, patient monitoring system 2 may output, for display at display 16, an indication of the amount of analgesic to administer to patient 6 or a more general instruction or suggestion to the clinician to increase or otherwise adjust the amount of analgesic.

In some examples, patient monitoring system 2 may be able to control analgesic administration device 18 to administer analgesic to patient 6 without user intervention. As such, in order to provide an indication to adjust an amount of analgesic to administer to patient 6, patient monitoring system 2 may output a signal to analgesic administration device 18 to direct analgesic administration device 18 to increase or otherwise adjust the amount of analgesic to administer to patient 6. Analgesic administration device 18 may, in response to receiving the signal, increase or otherwise adjust the amount of analgesic to administer to patient 6.

In some examples, patient monitoring system 2 may determine how much to adjust the amount of analgesic administered to patient 6 based at least in part on the amount of force exerted by surgical device 10, such as to make the incision or to intubate or extubate patient 6. As described above, in some examples, patient monitoring system 2 may include one or more sensors 12 attached to one or more surgical devices 10 that measure the amount of force exerted by one or more surgical devices 10 to make incisions in patient 6 or to intubate or extubate patient 6. As such, in some examples, the indication of robotic surgical system 8 making the incision in patient 6 received from robotic surgical system 8 may include an indication of the amount of force exerted by one or more surgical devices 10 to make incisions in patient 6. Patient monitoring system 2 may accordingly determine how much to increase the amount of analgesic administered to patient 6 based at least in part on the indication of the amount of force exerted by one or more surgical devices 10.

Because the amount of forced exerted by one or more surgical devices 10 may correspond to the surgical stress experienced by the patient, patient monitoring system 2 may increase the amount of analgesic administered to patient 6 (or provide an instruction via display 16 regarding the same) by a relatively smaller amount if the amount of force exerted by one or more surgical devices 10 on patient 6 is relatively small. Conversely, patient monitoring system 2 may increase the amount of analgesic administered to patient 6 (or provide an instruction via, display 16 regarding the same) by a relatively larger amount if the amount of force exerted by one or more surgical devices 10 on patient 6 is relatively large.

In some examples, patient monitoring system 2 may determine how much to adjust the amount of analgesic administered to patient 6 based at least in part on the physiological feature of patient 6 being incised by one or more surgical devices 10. As described above, robotic surgical system 8 may use image recognition to determine the physiological feature being incised. As such, in some examples, the indication of the surgical event received from robotic surgical system 8 may include an indication of the physiological feature of patient 6 being incised by one or more surgical devices 10, and patient monitoring system 2 may determine how much to increase the amount of analgesic administered to patient 6 based at least in part on the physiological feature of patient 6 being incised.

Making incisions on different physiological features of patient 6 may cause patient 6 to experience different amounts of surgical stress. For example, making an incision on the lymph nodes of patient 6 may cause patient 6 more surgical stress compared with making an incision on the skin of patient 6. As such, patient monitoring system 2 may adaptively determine how much to increase the amount of analgesic administered to patient 6 based on the physiological feature of patient 6 being incised by surgical device 10.

In some examples, patient monitoring system 2 may determine how much to adjust the amount of analgesic administered to patient 6 and/or whether to adjust the amount of analgesic administered to patient 6 based on the current level of analgesic administered to patient 6 and/or the total amount of analgesic administered to patient 6 during the current medical procedure. In some examples, patient monitoring system 2 may limit the amount of analgesic administered to patient 6 at any point in time to a specified analgesic level. As such, patient monitoring system 2 may increase the amount of analgesic administered to patient 6 at a point in time to no more than the specified analgesic level. If patient monitoring system 2 determines that increasing the amount of analgesic administered to patient 6 would cause the amount of analgesic administered to patient 6 to rise above the specified analgesic level, then patient monitoring system 2 may refrain from increasing the amount of analgesic administered to patient 6 or providing an instruction to increase the amount of analgesic via display 16.

In some examples, patient monitoring system 2 may determine how much to adjust the amount of analgesic administered to patient 6 and/or whether to adjust the amount of analgesic administered to patient 6 based on the total amount of analgesic administered to patient 6 during the course of the surgery or other medical procedure. For example, the total amount of analgesic administered to patient 6 over the course of the surgery may not exceed a total analgesic limit. If patient monitoring system 2 determines that increasing the amount of analgesic administered to patient 6 would cause the total amount of analgesic administered to patient 6 over the course of the surgery to rise above the total analgesic limit, then patient monitoring system 2 may refrain from increasing the amount of analgesic administered to patient 6 providing an instruction to increase the amount of analgesic via display 16.

Patient monitoring system 2 may determine how much to increase the amount of analgesic administered to patient 6 using any techniques described above alone or in combination with each other.

The techniques described herein may provide one or more advantages. By communicating with robotic surgical system 8, patient monitoring system 2 may be able to determine when robotic surgical system 8 is making incisions in patient 6 or performing any other medical procedure on patient 6 and may be to better determine which of the occurrences of nociception events of patient 6 detected by patient monitoring system correspond to surgical stress caused by incisions being made in patient 6 and which of the occurrences of nociception events of patient 6 are false positives.

Being able to identify nociception events that are false positives may enable patient monitoring system 2 to decrease the number of times patient monitoring system 2 increases the amount of analgesic that is administered to patient 6, thereby decreasing the total amount of analgesic that patient monitoring system 2 administers to patient 6 during surgery while still being able to effectively dampen excessive surgical stress experienced by patient 6. Decreasing the total amount of analgesic that patient monitoring system 2 administers to patient 6 during surgery may decrease the amount of side effects of the analgesia experienced by patient 6 after surgery and may decrease the amount of time that patient 6 experiences such side effects.

Further, administering a more proper amount of analgesic to the patient (e.g., better corresponding to surgical stress experienced by patient 6 during surgery using the techniques described herein may have one or more beneficial outcomes, such as leading to reductions in 1) opioid administration during and after surgery, 2) post-operative pain scores, 3) the length of the hospital stay, and/or 4) post-operative complications.

Figure 2A:
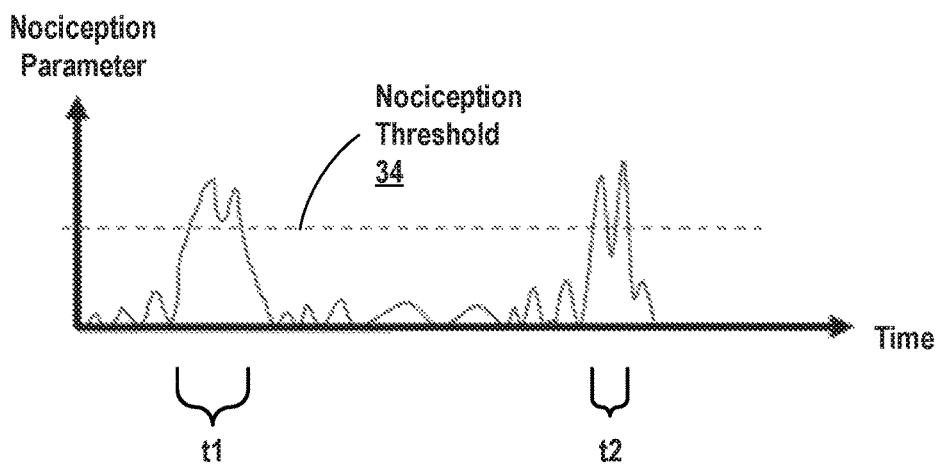
FIGS. 2A-2B illustrate an example of a monitored nociception parameter of a patient over time.
Figure 2B:
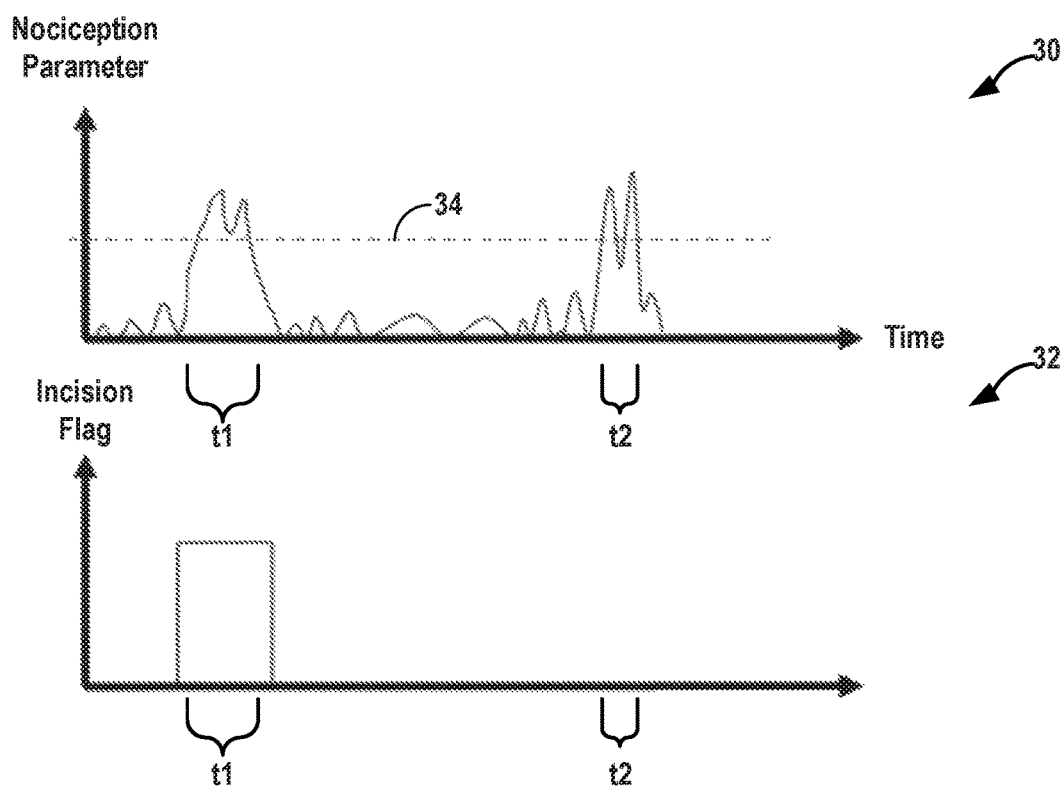

FIGS. 2A-2B illustrate example nociception parameter of patient 6 over time during surgery. As shown in FIG. 2A, patient monitoring system 2 may output, for display at display 16, time graph 30 that is a visual representation of the nociception parameter of patient 6 over time during surgery, as monitored by nociception monitor 4. Time graph 30 may include nociception threshold 34 so that time graph 30 may visually represent when the nociception parameter of patient 6 is greater than or equal to nociception threshold 34. In the example of FIG. 2A, the nociception parameter may be greater than or equal to nociception threshold 34 during time period t1 and during time period t2. As such, in time graph 30, nociception events for patient 6 are detected during time period t1 and time period t2. However, a clinician or patient monitoring system 2 may not be able to determine, from time graph 30, whether the occurrences of nociception events during time periods t1 and t2 are due to an incision that is made in patient 6 during time periods t1 and t2 or whether the occurrences of nociception events during time periods t1 and t2 are false positives caused by noise.

As shown in FIG. 2B, patient monitoring system 2 may output, for display at display 16, time graph 30 that is a visual representation of the nociception parameter of patient 6 over time, as monitored by nociception monitor 4 as well as time graph 32 that is a visual representation of the surgical event flag over time. As can be seen in time graph 32, the surgical event flag is set (e.g., has a non-zero value) during the time period t1 and is not set (e.g., has a value of zero) during the time period t2. As such, because the surgical event flag is set during time period t1, the time at which the nociception event occurs during time t1 corresponds to the time at which the surgical event occurs, and time graphs 30 and 32 may indicate, such as to a clinician or to patient monitoring system 2, that the occurrence of the nociception event during time period t1 is caused, for example, by an incision that is made in patient 6 during time period t1. Conversely, because the surgical event flag is not set during time period t2, time graphs 30 and 32 may indicate, such as to a clinician or patient monitoring system 2, that the occurrence of the nociception event during time period t2 is a false positive that is not caused by robotic surgical system 8 making an incision in patient 6 or by robotic surgical system 8 intubating or extubating patient 6 during time period t2. As such, based on the information presented by time graphs 30 and 32, patient monitoring system 2 may increase the amount of analgesic administered to patient 6 during time period t1 and may refrain from increasing the amount of analgesic administered to patient 6 during time period t2.

Figure 3:
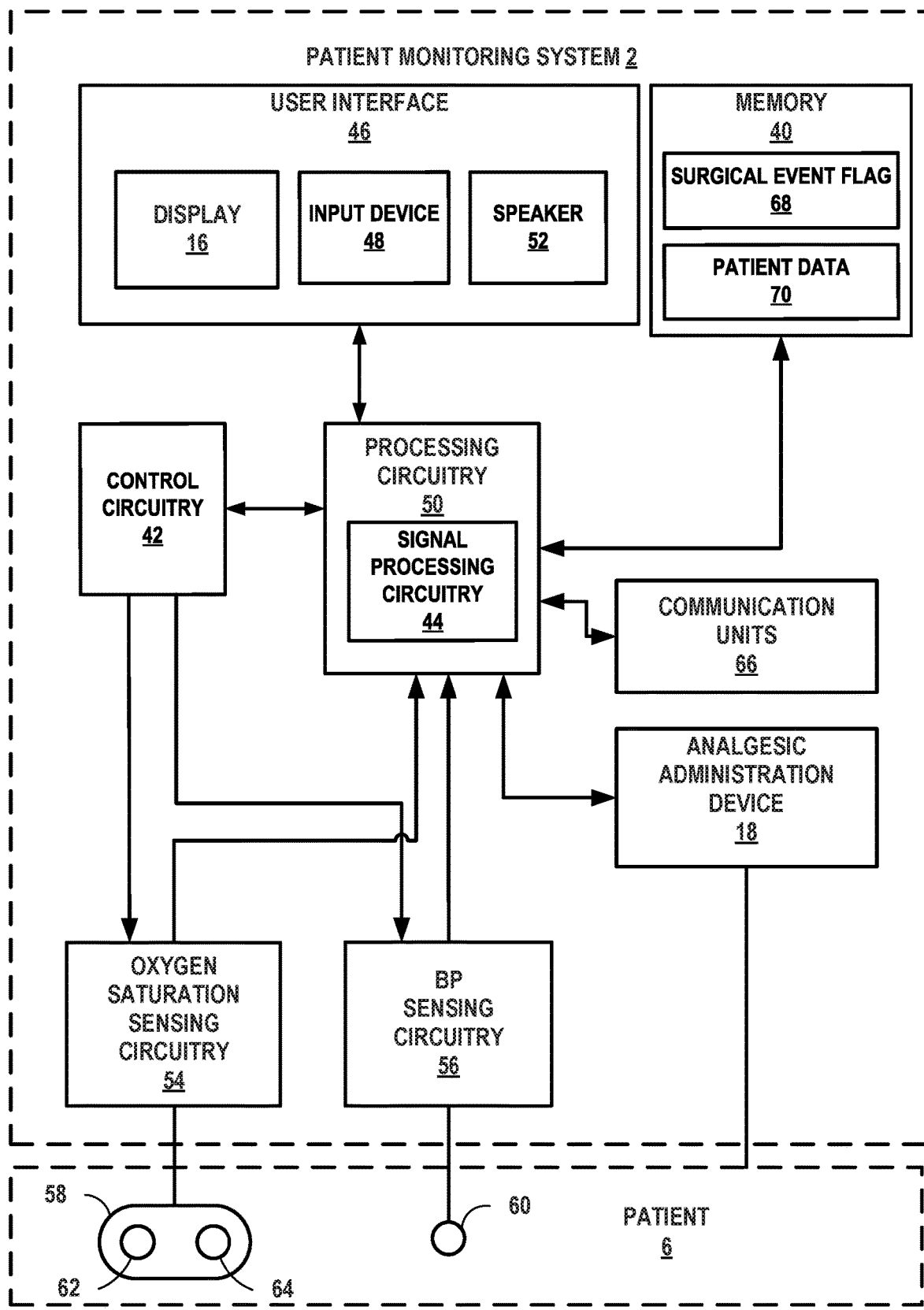
FIG. 3 is a block diagram illustrating the patient monitoring system of FIG. 1.

FIG. 3 is a block diagram illustrating an example of the patient monitoring system 2 of FIG. 1. As shown in FIG. 3, patient monitoring system 2 may include memory 40, control circuitry 42, user interface 46, processing circuitry 50, sensing circuitry 54 and 56, sensing devices 58 and 60, and one or more communication units 66. In the example shown in FIG. 1, user interface 46 may include display 16, input device 48, and/or speaker 52, which may be any suitable audio device including circuitry configured to generate and output a sound and/or noise. In some examples, patient monitoring system 2 may be configured to determine and output (e.g., for display at display 16) the nociception parameter of a patient 6 during surgery performed via robotic surgical system 8.

Processing circuitry 50, as well as other processors, processing circuitry, controllers, control circuitry, and the like, described herein, may include one or more processors. Processing circuitry 50 and control circuitry 42 may each include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 50 and/or control circuitry 42 may include multiple components, such as any combination of one or more microprocessors, one or more DSPs, one or more ASICs, or one or more FPGAs, as well as other discrete or integrated logic circuitry, and/or analog circuitry.

Control circuitry 42 may be operatively coupled to processing circuitry 50. Control circuitry 42 is configured to control an operation of sensing devices 58 and 60. In some examples, control circuitry 42 may be configured to provide timing control signals to coordinate operation of sensing devices 58 and 60. For example, sensing circuitry 54 and 56 may receive from control circuitry 42 one or more timing control signals, which may be used by sensing circuitry 54 and 56 to turn on and off respective sensing devices 58 and 60, such as to periodically collect calibration data using sensing devices 58 and 60. In some examples, processing circuitry 50 may use the timing control signals to operate synchronously with sensing circuitry 54 and 56. For example, processing circuitry 50 may synchronize the operation of an analog-to-digital converter and a demultiplexer with sensing circuitry 54 and 56 based on the timing control signals.

One or more communication units 66 may be operable to communicate with robotic surgical system 8 via one or more networks by transmitting and/or receiving network signals on the one or more networks such as the Internet, a Wide Area Network, a Local Area Network, and the like. Examples of one or more communication units 66 include a network interface card (e.g. such as an Ethernet card), an optical transceiver, a radio frequency transceiver, or any other type of device that can send and/or receive information. Other examples of one or more communication units 66 may include Near-Field Communications (NFC) units, Bluetooth® radios, short wave radios, cellular data radios, wireless network (e.g., Wi-Fi®) radios, as well as universal serial bus (USB) controllers.

Memory 40 may be configured to store, for example, surgical event flag 68 and patient data 70. For example, when processing circuitry 50 receives, via one or more communication units 66, an indication of robotic surgical system 8 making an incision on patient 6 from robotic surgical system 8, processing circuitry 50 may set surgical event flag 68, such as by storing a value for surgical event flag 68 that is indicative of robotic surgical system 8 making an incision on patient 6. Processing circuitry 50 may also store various data associated with patient 6 in patient data 70. For example, processing circuitry 50 may store the nociception parameter of patient 6, a predetermined nociception threshold, the total amount of analgesic administered to patient 6, a current level of analgesic being administered to patient 6, and the like in patient data 70 in memory 40. The predetermined nociception threshold can be specific to patient 6 or used for a population of patients.

In some examples, the predetermined nociception threshold may be adjustable. That is, processing circuitry 50 may be able to set different nociception thresholds for different patients, different types of surgeries or medical procedures, different surgical events, and the like, different physiological features of patient 6 being incised, and the like.

In some examples, memory 40 may store program instructions. The program instructions may include one or more program modules that are executable by processing circuitry 50. When executed by processing circuitry 50, such program instructions may cause processing circuitry 50 to provide the functionality ascribed to it herein. The program instructions may be embodied in software, firmware, and/or RAMware. Memory 40 may include any one or more of volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

User interface 46 may include a display 16, an input device 48, and a speaker 52. In some examples, user interface 46 may include fewer or additional components. User interface 46 is configured to present information to a user (e.g., a clinician). For example, user interface 46 and/or display 16 may include a monitor, cathode ray tube display, a flat panel display such as a liquid crystal (LCD) display, a plasma display, a light emitting diode (LED) display, and/or any other suitable display. In some examples, user interface 46 may be part of a multiparameter monitor (MPM) or other physiological signal monitor used in a clinical or other setting, a personal digital assistant, mobile phone, tablet computer, laptop computer, any other suitable computing device, or any combination thereof, with a built-in display or a separate display.

In some examples, processing circuitry 50 may be configured to present, by user interface 46, such as display 16, a graphical user interface to a user. The graphical user interface can include information regarding the delivery of analgesic or anesthesia to patient 6, one or more sensed nociception parameters, and the like. For example, the graphical user interface may include time graphs 30 and 32 of FIGS. 2A-2B of the nociception parameter of patient 6 over time and the value of surgical event flag 68 over time, or combinations thereof via display 16. In some examples, the graphical user interface can also include an instruction or suggestion to a clinician to administer additional analgesics or anesthesia. User interface 46 may also include means for projecting audio to a user, such as speaker 52.

In some examples, processing circuitry 50 may also receive input signals from additional sources (not shown), such as a user. For example, processing circuitry 50 may receive from input device 48, such as a keyboard, a mouse, a touch screen, buttons, switches, a microphone, a joystick, a touch pad, or any other suitable input device or combination of input devices, an input signal. The input signal may contain information about patient 6, such as physiological parameters, treatments provided to patient 6, or the like. Additional input signals may be used by processing circuitry 50 in any of the determinations or operations it performs in accordance with processing circuitry 50.

In some examples, processing circuitry 50 and user interface 46 may be part of the same device or supported within one housing (e.g., a computer or monitor). In other examples, processing circuitry 50 and user interface 46 may be separate devices configured to communicate through a wired connection or a wireless connection.

Sensing circuitry 54 and 56 is configured to receive signals ("physiological signals") indicative of physiological parameters from respective sensing devices 58 and 60 and communicate the physiological signals to processing circuitry 50. Sensing devices 58 and 60 may include any sensing hardware configured to sense a physiological parameter of a patient, e.g., indicative of a nociception response of patient 6. Example sensing hardware includes, but is not limited to, one or more electrodes, light sources, optical receivers, blood pressure cuffs, or the like. The sensed physiological signals may include signals indicative of physiological parameters from a patient, such as, but not limited to, blood pressure, blood oxygen saturation (e.g., pulse oximetry and/or regional oxygen saturation), blood volume, heart rate, heart rate variability, skin conductance, and respiration. For example, sensing circuitry 54 and 56 may include, but are not limited to, blood pressure sensing circuitry, blood oxygen saturation sensing circuitry, blood volume sensing circuitry, heart rate sensing circuitry, temperature sensing circuitry, electrocardiography (ECG) sensing circuitry, electroencephalogram (EEG) sensing circuitry, electromyogram (EMG) sensing circuitry or any combination thereof.

In some examples, sensing circuitry 54 and 56 and/or processing circuitry 50 may include signal processing circuitry 44 configured to perform any suitable analog conditioning of the sensed physiological signals. For example, sensing circuitry 54 and 56 may communicate to processing circuitry 50 an unaltered (e.g., raw) signal. Processing circuitry 50, e.g., signal processing circuitry 44, may be configured to modify a raw signal to a usable signal by, for example, filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof.

In some examples, the conditioned analog signals may be processed by an analog-to-digital converter of signal processing circuitry 44 to convert the conditioned analog signals into digital signals. In some examples, signal processing circuitry 44 may operate on the analog or digital form of the signals to separate out different components of the signals. In some examples, signal processing circuitry 44 may perform any suitable digital conditioning of the converted digital signals, such as low pass, high pass, band pass, notch, averaging, or any other suitable filtering, amplifying, performing an operation on the signal, performing any other suitable digital conditioning, or any combination thereof. In some examples, signal processing circuitry 44 may decrease the number of samples in the digital detector signals. In some examples, signal processing circuitry 44 may remove dark or ambient contributions to the received signal. Additionally or alternatively, sensing circuitry 54 and 56 may include signal processing circuitry 44 to modify one or more raw signals and communicate to processing circuitry 50 one or more modified signals.

In the example shown in FIG. 3, patient monitoring system 2 includes an oxygen saturation sensing device 58 (also referred to herein as blood oxygen saturation sensing device 58), which is configured to generate an oxygen saturation signal indicative of blood oxygen saturation within the venous, arterial, and/or capillary systems within a region of patient 6. For example, oxygen saturation sensing device 58 may include a sensor configured to non-invasively generate a plethysmography (PPG) signal. One example of such a sensor may be one or more oximetry sensors (e.g., one or more pulse oximetry sensors) placed at one or multiple locations on patient 6, such as at a fingertip of patient 6, an earlobe of patient 6, and the like.

In some examples, oxygen saturation sensing device 58 may be configured to be placed on the skin of patient 6 to determine regional oxygen saturation of a particular tissue region, e.g., the frontal cortex or another cerebral location of patient 6. Oxygen saturation sensing device 58 may include emitter 62 and detector 64. Emitter 62 may include at least two light emitting diodes (LEDs), each configured to emit at different wavelengths of light, e.g., red or near infrared light. As used herein, the term "light" may refer to energy produced by radiative sources and may include any wavelength within one or more of the ultrasound, radio, microwave, millimeter wave, infrared, visible, ultraviolet, gamma ray or X-ray electromagnetic radiation spectra. In some examples, light drive circuitry (e.g., within sensing device 58, sensing circuitry 54, control circuitry 42, and/or processing circuitry 50) may provide a light drive signal to drive emitter 62 and to cause emitter 62 to emit light. In some examples, the LEDs of emitter 62 emit light in the range of about 600 nanometers (nm) to about 1000 nm. In a particular example, one LED of emitter 62 is configured to emit light at about 730 nm and the other LED of emitter 62 is configured to emit light at about 810 nm. Other wavelengths of light may be used in other examples.

Detector 64 may include a first detection element positioned relatively "close" (e.g., proximal) to emitter 62 and a second detection element positioned relatively "far" (e.g., distal) from emitter 62. In some examples, the first detection elements and the second detection elements may be chosen to be specifically sensitive to the chosen targeted energy spectrum of emitter 62. Light intensity of multiple wavelengths may be received at both the "close" and the "far" detector 64. For example, if two wavelengths are used, the two wavelengths may be contrasted at each location and the resulting signals may be contrasted to arrive at an oxygen saturation value that pertains to additional tissue through which the light received at the "far" detector passed (tissue in addition to the tissue through which the light received by the "close" detector passed, the brain tissue), when it was transmitted through a region of a patient (e.g., a patient's cranium). In operation, light may enter detector 64 after passing through the tissue of patient 6, including skin, bone, other shallow tissue (e.g., non-cerebral tissue and shallow cerebral tissue), and/or deep tissue (e.g., deep cerebral tissue). Detector 64 may convert the intensity of the received light into an electrical signal. The light intensity may be directly related to the absorbance and/or reflectance of light in the tissue. Surface data from the skin and skull may be subtracted out, to generate an oxygen saturation signal for the target tissues over time.

Oxygen saturation sensing device 58 may provide the oxygen saturation signal to processing circuitry 50. Additional example details of determining oxygen saturation based on light signals may be found in commonly assigned U.S. Pat. No. 9,861,317, which issued on Jan. 9, 2018, and is entitled "Methods and Systems for Determining Regional Blood Oxygen Saturation." One example of such an oxygen saturation signal may be a plethysmography (PPG) signal.

In the example shown in FIG. 3, patient monitoring system 2 includes a blood pressure sensing device 60, which is configured to generate a blood pressure signal indicative of a blood pressure of patient 6. For example, blood pressure sensing device 60 may include a blood pressure cuff configured to non-invasively sense blood pressure or an arterial line configured to invasively monitoring blood pressure in an artery of patient 6. In some examples, the blood pressure signal may include at least a portion of a waveform of the acquisition blood pressure. Blood pressure sensing device 60 may be configured to generate a blood pressure signal indicative of the blood pressure of patient over time. Blood pressure sensing device 60 may provide the blood pressure signal to sensing circuitry 56, processing circuitry 50, or to any other suitable processing device, which may be part of patient monitoring system 2 or a device separate from patient monitoring system 2, such as another device co-located with patient monitoring system 2 or remotely located relative to patient monitoring system 2.

In operation, blood pressure sensing device 60 and oxygen saturation sensing device 58 may each be placed on the same or different parts of the body of patient 6. For example, blood pressure sensing device 60 and oxygen saturation sensing device 58 may be physically separate from each other and may be separately placed on patient 6. As another example, blood pressure sensing device 60 and oxygen saturation sensing device 58 may in some cases be supported by a single sensor housing. One or both of blood pressure sensing device 60 or oxygen saturation sensing device 58 may be further configured to measure other patient parameters, such as hemoglobin, respiratory rate, respiratory effort, heart rate, saturation pattern detection, response to stimulus such as bispectral index (BIS) or electromyography (EMG) response to electrical stimulus, or the like. While an example patient monitoring system 2 is shown in FIG. 3, the components illustrated in FIG. 3 are not intended to be limiting. Additional or alternative components and/or implementations may be used in other examples.

Processing circuitry 50 may be configured to receive one or more physiological signals generated by sensing devices 58 and 60 and sensing circuitry 54 and 56. The physiological signals may include a signal indicating blood pressure and/or a signal, such as a PPG signal, indicating oxygen saturation. Processing circuitry 50 may be configured to obtain the nociception parameter for patient 6 over time while patient 6 is in surgery by continuously determining, based on the one or more physiological signals generated by sensing devices 58 and 60, the nociception parameter for patient 6. For example, the nociception parameter may be a value between 0 to 100 that indicates the amount of surgical stress experienced by patient 6 during surgery. As processing circuitry 50 receives the one or more physiological signals during surgery of patient 6, processing circuitry 50 may be able to continuously determine, based on the one or more physiological signals, the nociception parameter for patient 6 over time. As such processing circuitry 50, sensing circuitry 54 and 56, and sensing devices 58 and 60 may together implement nociception monitor 4 of patient monitoring system 2 shown in FIG. 1. In other examples, processing circuitry 50 may be configured to obtain the nociception parameter for patient 6 via one or more external devices. For example, processing circuitry 50 may be configured to communicate, via communication units 66, with an external device that sends the nociception parameter for patient 6 to processing circuitry 50.

In accordance with aspects of the present disclosure, patient monitoring system 2 is configured to determine, based at least in part on the nociception parameter of patient 6 during surgery, whether to adjust the amount of analgesic administered to patient 6. Processing circuitry 50 may receive, via one or more communication units 66 and from robotic surgical system 8, an indication of a surgical event from robotic surgical system 8. In some examples, the indication of a surgical event may be an indication of an action performed by robotic surgical system 8, such as an indication of robotic surgical system 8 making an incision in patient 6 or an indication of robotic surgical system 8 intubating or extubating patient 6.

In some examples, the indication of the surgical event may include an indication of an amount of force sensed by a sensor (e.g., one or more sensors 12) on a surgical device (e.g., one or more surgical devices 10) of robotic surgical system 8 to perform an action on patient 6, such as to make the incision on patient 6 or to intubate or extubate patient 6. In some examples, the indication of robotic surgical system 8 making the incision in patient 6 may include an indication of a physiological feature of patient 6 being incised by robotic surgical system 8.

In response to receiving the indication of the surgical event, processing circuitry 50 may set surgical event flag 68 to indicate the occurrence of the surgical event. For example, processing circuitry 50 may store a value for surgical event flag 68 in memory 40 to indicate the occurrence of the surgical event. If the indication of the surgical event includes an indication of an amount of force sensed by a sensor on a surgical device of robotic surgical system 8 to make the incision on patient 6 or to intubate or to extubate patient 6, then processing circuitry 50 may store a value for surgical event flag 68 that is indicative of the amount of force sensed by the sensor. If the indication of the surgical event includes an indication of the physiological feature of patient 6 being incised by robotic surgical system 8, then processing circuitry 50 may store a value for surgical event flag 68 that is indicative of the physiological feature of patient 6 being incised by robotic surgical system 8.

As processing circuitry 50 monitors the nociception parameter of patient 6, processing circuitry 50 may compare the nociception parameter of patient 6 to a nociception threshold (stored by memory 40 or a memory of another device) for patient 6 to detect a nociception event. For example, processing circuitry 50 may determine whether the nociception parameter of patient 6 is greater than or equal to the nociception threshold for patient 6. Processing circuitry 50 may, in response to determining that the nociception parameter of patient 6 is greater than or equal to a nociception threshold for patient 6, determine that a nociception event has occurred.

Processing circuitry 50 may determine whether the surgical event corresponds to the occurrence of the nociception event. That is, processing circuitry 50 may determine whether the surgical event corresponds in time to the nociception parameter of patient 6 to be greater than or equal to the nociception threshold for patient 6.

To determine whether the surgical event corresponds to the nociception event, processing circuitry 50 may determine whether the nociception event occurred while surgical event flag 68 is set. For example, processing circuitry 50 may determine whether the nociception parameter of patient 6 is greater than or equal to the nociception threshold for patient 6 while surgical event flag 68 is set. If processing circuitry 50 determines that the nociception parameter of patient 6 is greater than or equal to the nociception threshold for patient 6 while surgical event flag 68 is set, then processing circuitry 50 may determine that the surgical event corresponds to the nociception event.

In some examples, processing circuitry 50 may, in response to determining that the surgical event corresponds to the nociception event, output a notification via user interface 46. The notification can be any suitable visual, audible, somatosensory, or any combination thereof, notification that indicates the nociception event was detected. In some examples, the notification includes an indication to adjust an amount of analgesic to administer to patient 6. That is, in response to determining that robotic surgical system making the incision on patient 6 causing patient 6 to experience excess surgical stress, processing circuitry 50 may cause analgesic administration device 18 to increase the amount of analgesic administered to patient 6 to dampen the surgical stress experienced by patient 6 by directly controlling analgesic administration device 18 or by generating a notification that causes a clinician to control analgesic administration device 18. Example analgesics that analgesic administration device 18 can administer include, but are not limited to, one or more of remifentanil, alfentanil, and fentanyl.

In some examples, instead of determining that nociception event occurred while surgical event flag 68 is set, processing circuitry 50 may determine a sharp rise (e.g., a specified amount of increase in the nociception parameter over a specified amount of time) in the nociception parameter of patient 6 over time while surgical event flag 68 is set. Thus, in some examples, even if the nociception parameter of patient 6 is not greater than or equal to the nociception threshold while surgical event flag 68 is set, processing circuitry 50 may determine that a sharp rise in nociception parameter of patient 6 over time while surgical event flag 68 is set is a nociception event indicative of the surgical event causing excess surgical stress experienced by patient 6. Processing circuitry 50 may, in response to determining the sharp rise in the nociception parameter of patient 6 over time while surgical event flag 68 is set, output the notification, e.g., to notify a clinician and/or to provide an indication to increase an amount of analgesic to administer to patient 6.

In some examples, a nociception parameter may specify a base nociception threshold that is less than the nociception parameter. If a nociception parameter for patient 6 is below the base nociception threshold, then processing circuitry may refrain from outputting the notification via user interface 46. As such, in some examples, if the highest nociception parameter in a sharp rise in nociception parameter of patient 6 over time detected by processing circuitry 50 is below the base nociception threshold, then processing circuitry 50 may refrain from providing an indication to adjust an amount of analgesic to administer to patient 6 or providing another output via user interface 46.

In some examples, to provide an indication to adjust an amount of analgesic to administer to patient 6, processing circuitry 50 may output, for display at display 16, an indication to increase an amount of analgesic to administer to patient 6, so that a clinician that views display 16 may therefore control analgesic administration device 18 to adjust the amount of analgesic administered to patient 6.

In some examples, to provide an indication to adjust an amount of analgesic to administer to patient 6, processing circuitry 50 may send, to analgesic administration device 18, the indication to adjust the amount of analgesic administered to patient 6. Analgesic administration device 18 may, in response to receiving the indication, adjust the amount of analgesic that analgesic administration device 18 delivers to patient 6. In this way, patient monitoring system 2 may act as an automated analgesic administration system.

In some examples, processing circuitry 50 may determine how much to adjust the amount of analgesic administered to patient 6 based at least in part on the amount of force associated with the surgical event. For example the value stored for surgical event flag 68 in memory 40 may be indicative of the amount of force sensed by the sensor. If the value indicative of the amount of force sensed by the sensor is relatively low, e.g., lower than a predetermined force threshold stored by memory 40 or a memory of another device, thereby indicating a relatively low amount of force sensed by the sensor, then processing circuitry 50 may increase the amount of analgesic administered to patient 6 by a relatively smaller amount. If the value indicative of the amount of force sensed by the sensor is relatively high, e.g., greater than or equal to the predetermined force threshold, thereby indicating a relatively high amount of force sensed by the sensor, then processing circuitry 50 may increase the amount of analgesic administered to patient 6 by a relatively greater amount. Processing circuitry 50 may therefore provide an indication of how much to increase the amount of analgesic administered to patient 6, such as to analgesic administration device 18 to control the amount of analgesic administered to patient 6.

In some examples, processing circuitry 50 may determine how much to adjust the amount of analgesic administered to patient 6 based at least in part on the physiological feature of patient 6 being incised by robotic surgical system 8. For example, the value stored for surgical event flag 68 in memory 40 may be indicative of the physiological feature of patient 6 being incised by robotic surgical system 8. Different physiological features of patient 6 may cause different amounts of surgical stress when incised. For example, memory 40 may store a lookup table of physiological features and associated amounts of surgical stress.

As such, processing circuitry 50 may determine the physiological feature of patient 6 being incised from the value for surgical event flag 68, look up the amount of surgical stress caused by incising the physiological feature in memory 40, and determine how much to increase the amount of analgesic administered to patient 6 based on the amount of surgical stress caused by incising the physiological feature. For example, if making an incision on the physiological feature causes relatively low surgical stress, then processing circuitry 50 may increase the amount of analgesic administered to patient 6 by a relatively smaller amount. If making an incision on the physiological feature causes relatively high surgical stress, then processing circuitry 50 may increase the amount of analgesic administered to patient 6 by a relatively higher amount. Processing circuitry 50 may therefore provide an indication of how much to adjust the amount of analgesic administered to patient 6, such as to analgesic administration device 18 to control the amount of analgesic administered to patient 6.

In some examples, processing circuitry 50 may determine how much to adjust the amount of analgesic administered to patient 6 based on at least one of: a current amount of analgesic being administered to patient 6 and a total amount of analgesic administered to patient 6 during surgery. In some examples, the amount of analgesic being administered to patient 6 at any point in time may not exceed a specified analgesic level. Thus, processing circuitry 50 may determine whether increasing the current amount of analgesic administered to patient 6 may cause the amount of analgesic administered to exceed the specified analgesic level and, if so, to reduce the increase in the amount of analgesic administered to patient 6 so that the amount of analgesic administered to patient 6 remains below the specified analgesic level.

In some examples, it may be desirable to limit to the total amount of analgesic administered to patient 6 during surgery. Thus, in some examples, processing circuitry 50 may determine whether increasing the current amount of analgesic administered to patient 6 may cause the total amount of analgesic administered to patient 6 during surgery to exceed the limit and, if so, to reduce the increase in the amount of analgesic administered to patient 6 so that the amount of analgesic administered to patient 6 does not cause the total amount of analgesic administered to patient 6 during surgery to exceed the limit.

In some examples, in response to making an incision on patient 6, robotic surgical system 8 may pause making any further incisions on patient 6 until analgesic administration device 18 has increased the amount of analgesic administered to patient 6 and until the additional analgesic has had time to take effect to reduce the surgical stress of patient 6. As such, in some examples, processing circuitry 50 may, in response to analgesic administration device 18 increasing the amount of analgesic administered to patient 6, send, to robotic surgical system, an indication to restart making further incisions in patient 6.

The components of patient monitoring system 2 that are shown and described as separate components are shown and described as such for illustrative purposes only. In some examples the functionality of some of the components may be combined in a single component. For example, the functionality of processing circuitry 50 and control circuitry 42 may be combined in a single processor system. Additionally, in some examples the functionality of some of the components of patient monitoring system 2 shown and described herein may be divided over multiple components or over multiple devices. For example, some or all of the functionality of control circuitry 42 may be performed in processing circuitry 50, or sensing circuitry 54 and 56. In other examples, the functionality of one or more of the components may be performed in a different order or may not be required.

Figure 4:
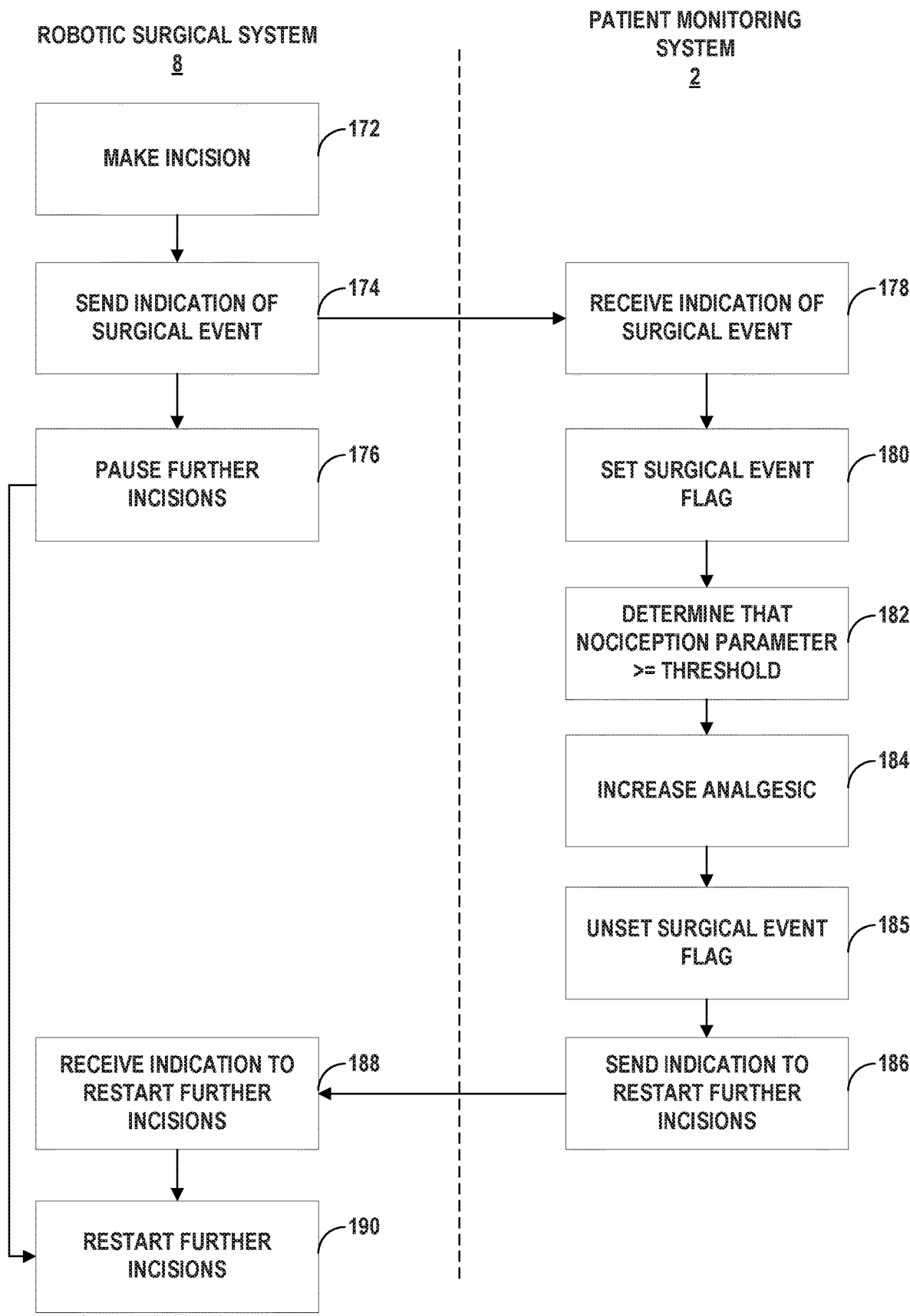
FIG. 4 is a flow diagram illustrating an example process performed by a robotic surgical system and a patient monitoring system to determine whether to adjust the amount of analgesic administered to the patient.

FIG. 4 is a flow diagram illustrating an example process performed by robotic surgical system 8 and patient monitoring system 2 to determine whether to adjust the amount of analgesic administered to patient 6. FIG. 4 is described with respect to FIG. 1, but can be performed using other similar systems.

As shown in FIG. 4, in the process of performing surgery on patient 6, robotic surgical system 8 may make an incision in patient 6 using one or more surgical devices 10 (172). In response to making the incision on patient 6, robotic surgical system 8 may send an indication of a surgical event, such as an indication that robotic surgical system 8 has made an incision in patient 6, to patient monitoring system 2. In some examples, robotic surgical system 8 may send to patient monitoring system 2 an indication of the surgical event at the start of making the incision and may, once robotic surgical system 8 has finished making the incision, also send an indication that the surgical event has ended. In some examples, while robotic surgical system 8 makes the incision in patient 6, robotic surgical system may continuously, such as every millisecond, every 5 milliseconds, and the like, send to patient monitoring system 2 an indication of the surgical event until robotic surgical system 8 has finished making the incision. In other examples, robotic surgical system 8 may send to patient monitoring system 2 an indication that robotic surgical system 8 has made an incision in patient 6 at the time after the incision is completely formed.

In some examples, one or more sensors 12 on one or more surgical devices 10 may sense the amount of force exerted by one or more surgical devices 10 to make the incision or to intubate or extubate patient 6, and robotic surgical system 8 may send an indication of the amount of force sensed by one or more sensors 12 to patient monitoring system 2. For example, robotic surgical system 8 may translate the amount of force sensed by one or more sensors 12 to a value within a range of values indicative of the amount of force sensed by one or more sensors 12, and may send such a value to patient monitoring system 2. For example, robotic surgical system 8 may translate the amount of force sensed by one or more sensors 12 to a value within a range of values, such as from 1 to 10, where a value of 1 may indicate the smallest amount of force sensed by one or more sensor 12 and a value of 10 may indicate the greatest amount of force sensed by one or more sensor 12. Robotic surgical system 8 can use other techniques for indicating the forced sensed by one or more sensors 12 in other examples, e.g., sending the raw or digitized sensor signal to processing circuitry 50 of patient monitoring system 2.

In some examples, camera 14 may capture one or more images of the physiological feature of patient 6 being incised by one or more surgical devices 10. Robotic surgical system 8 may process the one or more images captured by camera 14, such as by performing one or more image recognition algorithms, to determine, based on the one or more images captured by camera 14. For example, robotic surgical system 8 may perform image recognition to determine whether patient 6's lymph nodes, lung, heart muscle, and the like is being incised, and may send an indication of the physiological feature of patient 6 being incised to patient monitoring system 2.

In some examples, robotic surgical system 8 may, after making the incision, pause making any further incisions on patient 6 to provide time for the increase in the amount of analgesic administered to patient 6 to take effect (176). In some examples, robotic surgical system 8 may pause making any further incisions on patient 6 for a specified period of time, such as 5 seconds, 10 seconds, and the like. In some examples, robotic surgical system 8 may pause making any further incisions on patient 6 until robotic surgical system 8 receives, from patient monitoring system 2, an indication to continue making further incisions on patient 6.

Processing circuitry 54 of patient monitoring system 2 may receive, from robotic surgical system 2, the indication of the surgical event (178) and may, in response to receiving the indication, set a surgical event flag to indicate that the surgical event has occurred (180). For example, processing circuitry 54 may change the value of a surgical event flag from 0 to 1 to set the surgical event flag. In some examples, if the indication received by patient monitoring system 2 includes an indication of the amount of force sensed by one or more sensors 12, then processing circuitry 54 may change the value of the surgical event flag to a value that corresponds to the indicated amount of force. In some examples, if the indication received by patient 2 includes an indication of the physiological feature of patient 6 being incised, then processing circuitry 54 may change the value of the surgical event flag to a value indicative of the physiological feature of patient 6 being incised.

Because patient monitoring system 2 has set the surgical event flag to indicate that robotic surgical system 8 has made an incision in patient 6, processing circuitry 54 may be able to determine that nociception events detected while the surgical event flag is set are not false positive indications of a severe nociceptive stimulus caused by, for example, noise. Thus, if processing circuitry 54 determines the nociception parameter for patient 6 is greater than or equal to the nociception threshold while the surgical event flag is set (182), then analgesic administration device 18 of patient monitoring system 2 may increase the amount of analgesic administered to patient 6 to dampen down the nociception response of patient 6 caused by making incision (184). For example, a clinician may control analgesic administration device 18 to modify the amount of analgesic administered to patient 6 or processing circuitry 54 may more directly control analgesic administration device 18, e.g., without user intervention or with limited user intervention (e.g., a clinician accepting a recommendation presented via user interface 46).

Patient monitoring system 2 may determine how much to increase the amount of analgesic administered to patient 6 based at least in part on the indication that robotic surgical system 8 has made an incision in patient 6 received from robotic surgical system 8. For example, if the indication that robotic surgical system 8 has made an incision in patient 6 received from robotic surgical system 8 includes an indication of the amount of force sensed by one or more sensors 12 on one or more surgical devices 10, then processing circuitry 54 may increase the amount of analgesic administered to patient 6 by a relatively higher amount if the amount of force indicated is relatively high, and may increase the amount of analgesic administered to patient 6 may a relatively lower amount if the amount of force indicated is relatively low. For example, if patient monitoring system 2 receives an indication of a value within a range of values indicative of the amount of force sensed by one or more sensors 12, such as a value that is between 1 and 10, then processing circuitry 54 may increase the amount of analgesic administered to patient 6 by a relatively higher amount if the received value is 10 compared with the increase in the amount of analgesic administered to patient 6 if the received value is 1.

In another example, the indication that robotic surgical system 8 has made an incision in patient 6 received from robotic surgical system 8 may include an indication of the physiological feature of patient 6 being incised. Patient monitoring system 2 may therefore determine how much to increase the amount of analgesic administered to patient 6 based at least in part on the physiological feature of patient 6 being incised. Incisions into different physiological features of patient 6 may cause different amounts of nociceptive responses. For example, making an incision in a lymph node may cause a different amount of nociceptive response compared to making an incision in a heart muscle. As such, processing circuitry 54 may cause the amount of analgesic administered to patient 6 to be increased by different levels for incisions being made to different physiological features of patient 6.

In some examples, in response to increasing the amount of analgesic administered to patient 6, processing circuitry 54 may unset the surgical event flag, such as by setting the value of the surgical event flag to a default value, such as 0, such as to indicate that patient monitoring system 2 has completed increasing the amount of analgesic administered to patient 6 in response to the incision made by robotic surgical system 8 (185). For example, processing circuitry 54 may unset the surgical event flag in response to the nociception parameter of patient 6 decreasing below the nociception threshold in response to the increase in the amount of analgesic administered to patient 6.

If robotic surgical system 8 had paused further incisions, then processing circuitry 54 may, in response to increasing the amount of analgesic administered to patient 6, send to robotic surgical system 8 an indication to restart making further incisions (186). Robotic surgical system 8 may receive the indication (188) and may, in response, restart making further incisions on patient 6 (190).

Figure 5A:
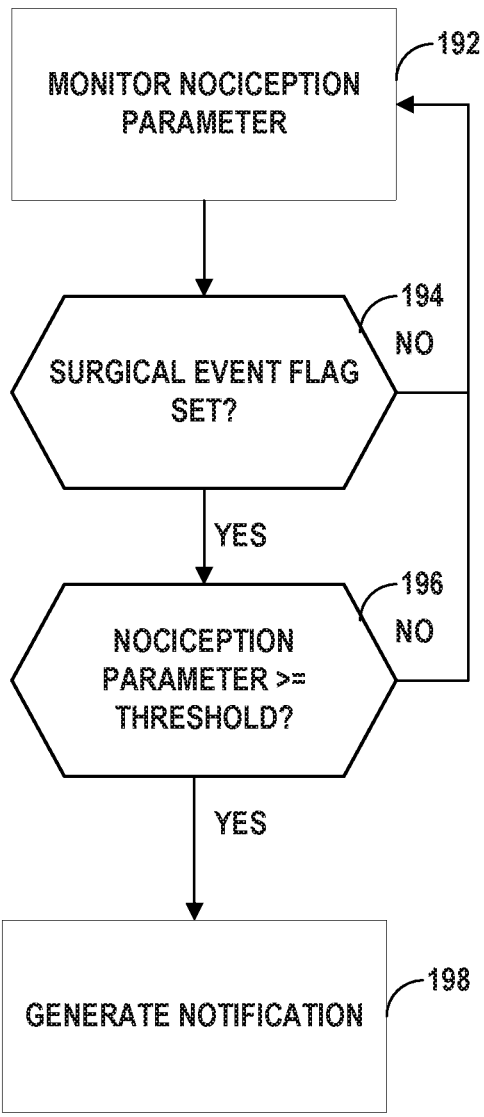
FIGS. 5A-5B are flow diagrams illustrating an example process performed by a patient monitoring system to adjust the amount of analgesic administered to a patient.
Figure 5B:
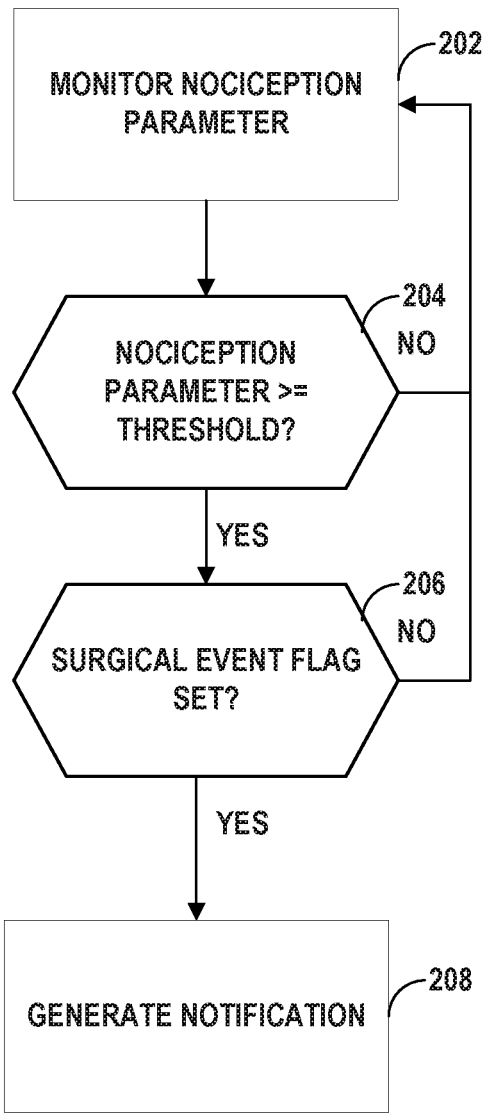

FIGS. 5A-5B are flow diagrams illustrating an example process performed by patient monitoring system 2 to adjust the amount of analgesic administered to patient 6. FIGS. 5A-5B are described with respect to FIG. 1, but can be performed by other similar systems in other examples.

As shown in FIG. 5A, nociception monitor 4 of patient monitoring system 2 may monitor the nociception parameter of patient 6 undergoing surgery over time to obtain the nociception parameter of patient 6 (192). In some examples, to help prevent false positive indications of a severe nociceptive stimulus caused by noise in the nociception parameters of patient 6, patient monitoring system 2 may not increase the amount of analgesic administered to patient 6 if a surgical event flag indicative of robotic surgical system 8 having made an incision in patient 6 is set. As such, patient monitoring system 2 may determine whether the surgical event flag is set (194).

If processing circuitry 54 of patient monitoring system 2 determines that the surgical event flag is not set ("NO" branch of block 194), then patient monitoring system 2 may return to monitoring and obtaining the nociception parameter of patient 6 (192). If processing circuitry 54 determines that the surgical event flag is set ("YES" branch of block 194), then processing circuitry 54 may compare the nociception parameter of patient 6 with the nociception threshold for patient 6 to detect a nociception event, such as by determining whether the nociception parameter of patient 6 is greater than or equal to the nociception threshold (196). If processing circuitry 54 determines that a nociception event has not occurred, such as if the nociception parameter is less than the nociception threshold ("NO" branch of block 196), then patient monitoring system 2 may return to monitoring the nociception parameter of patient 6 (192).

If processing circuitry 54 determines that a nociception event has occurred, such as if the nociception parameter is greater than or equal to the nociception threshold ("YES" branch of block 196), then processing circuitry 54 may determine that a surgical event corresponds to the nociception event and may generate a notification, e.g., to cause an increase in the amount of analgesic administered to patient 6 to dampen down the nociception response of patient 6 and hence reduce the surgical stress caused to patient 6 (198).

While FIG. 5A illustrates a technique in which patient monitoring system 2 determines whether the surgical event flag is set prior to determining whether a nociception event has occurred, the determination of whether the surgical event flag is set and the determination of whether a nociception event has occurred may occur in any order or may occur simultaneously. For example, as shown in FIG. 5B, nociception monitor 4 of patient monitoring system 2 may monitor the nociception parameter of patient 6 undergoing surgery over time (202). Processing circuitry 54 of patient monitoring system 2 may compare the nociception parameter of patient 6 with the nociception threshold for patient 6 to determine whether a nociception event has occurred, such as by determining whether the nociception parameter of patient 6 is greater than or equal to the nociception threshold (204). If processing circuitry 54 determines that the nociception event has not occurred, such as if the nociception parameter is not less than the nociception threshold ("NO" branch of block 204), then patient monitoring system 2 may return to monitoring the nociception parameter of patient 6 (202).

If processing circuitry 54 determines that a nociception event has occurred, such as if the nociception parameter is greater than or equal to the nociception threshold ("YES" branch of block 204), then processing circuitry 54 may determine whether the surgical event flag is set (206). If processing circuitry 54 determines that the surgical event flag is not set ("NO" branch of block 206), the patient monitoring system 2 may return to monitoring the nociception parameter of patient 6 (202). If processing circuitry 54 determines that the surgical event flag is set ("YES" branch of block 206), then patient monitoring system 2 may determine that a surgical event corresponds to the nociception event and may generate a notification, e.g., to cause an increase in the amount of analgesic administered to patient 6 to dampen down the nociception response of patient 6 and hence reduce the surgical stress caused to patient 6 (208).

Figure 6:
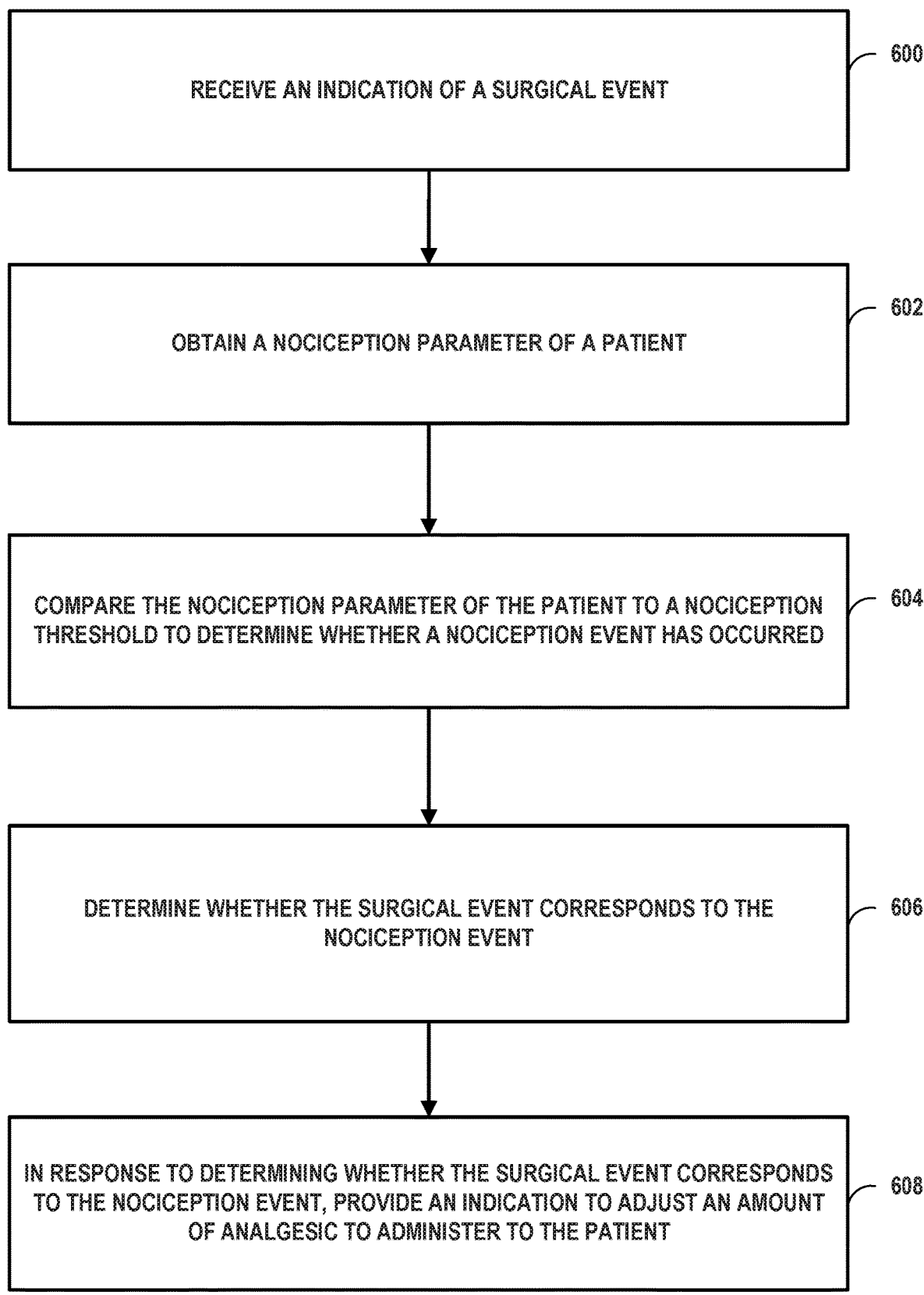
FIG. 6 is a flow diagram illustrating an example method of determining whether to increase the amount of analgesic administered to patient undergoing surgery by a robotic surgical system.

FIG. 6 is a flow diagram illustrating an example method of determining whether to increase the amount of analgesic administered to patient undergoing surgery by a robotic surgical system. Although FIG. 6 is described with respect to processing circuitry 50 of patient monitoring system 2 (FIGS. 1 and 3), in other examples, different processing circuitry, alone or in combination with processing circuitry 50, may perform any part of the technique of FIG. 6.

As shown in FIG. 6, processing circuitry 50 may receive, from a robotic surgical system 8, an indication of a surgical event (600). For example, the indication of the surgical event may include an indication of the robotic surgical system 8 making an incision in a patient 6 or an indication that patient 6 is being intubated or extubated. Processing circuitry 50 may obtain a nociception parameter of the patient 6 (602). For example, processing circuitry 50 may use nociception monitor 4 to monitor the nociception parameter of patient 6 over time during surgery to continuously obtain the latest nociception parameter of patient 6.

Processing circuitry 50 may compare the nociception parameter of the patient 6 with a nociception threshold 6 detect a nociception event (604). For example, processing circuitry 50 may detect a nociception event has occurred if the nociception parameter of the patient 6 is greater than or equal to the nociception threshold 6.

Processing circuitry 50 may determine whether the surgical event corresponds to the nociception event (606). That is, processing circuitry 50 may determine whether the nociception event indicates surgical stress in patent 6 is in response to the surgical event, Processing circuitry 50 may, in response to determinizing whether the surgical event corresponds to the nociception event, generate and present a notification via user interface

46 (FIG. 3), e.g., provide an indication to adjust an amount of analgesic administered to the patient 6 (608).

In some examples, processing circuitry 50 may, in response to receiving the indication of the surgical event set a surgical event flag 68. Processing circuitry 50 may, to determine whether the surgical event corresponds to the nociception event by determining whether the nociception parameter of the patient 6 is greater than or equal to the nociception threshold while the surgical event flag 68 is set. Processing circuitry 50 may output, for display at a display device 16, the nociception parameter of the patient 6 over time and a value of the surgical event flag 68 over time.

In some examples, the indication of the surgical event comprises an indication of an amount of force associated with the surgical event. For example, the amount of force associated with the surgical event may be the amount of force sensed by a sensor of a surgical device of a robotic surgical system 8 to make the incision on the patient 6 or may be the amount of force sensed by a sensor of a tracheal tube being intubated in patient 6 or being extubated from patient 6 Processing circuitry 50 may determine how much to adjust the amount of analgesic to administer to the patient 6 based at least in part on the amount of force surgical device associated with the surgical event.

In some examples, the indication of the surgical event, such as the indication of the robotic surgical system 8 making the incision on the patient 6, comprises an indication of a physiological feature of the patient 6 being incised by the robotic surgical system 8, and processing circuitry 50 may determine how much to adjust the amount of analgesic to administer to the patient 6 based at least in part on the physiological feature of the patient 6 being incised by the robotic surgical system 8.

In some examples, processing circuitry 50 may, to provide the indication to increase the amount of analgesic to administer to the patient 6, send, to an analgesia administration device 18, the indication to adjust the amount of analgesic administered to the patient 6.

In some examples, to compare the nociception parameter of the patient 6 to the nociception threshold, processing circuitry 50 may determine a sharp rise in the nociception parameter of the patient 6.

In some examples, processing circuitry 50 may, in response to providing the indication to adjust the amount of analgesic to administer to the patient 6, send, to a robotic surgical system 8, an indication to restart making further incisions.

In some examples, processing circuitry 50 may determine whether to adjust the amount of analgesic administered to the patient 6 based on a total amount of analgesic administered to the patient 6 during surgery.

The following examples may illustrate one or more aspects of the disclosure.

Example 1. A method comprising: receiving, by processing circuitry, an indication of a surgical event; obtaining, by the processing circuitry, a nociception parameter of a patient; comparing, by the processing circuitry, the nociception parameter of the patient to a nociception threshold to detect a nociception event; determining, by the processing circuitry, whether the surgical event corresponds to the nociception event; and in response to determining whether the surgical event corresponds to the nociception event, providing, by the processing circuitry, an indication to adjust an amount of analgesic administered to the patient.

Example 2. The method of Example 1, further comprising: in response to receiving the indication of the surgical event, setting, by the processing circuitry, a surgical event flag, wherein determining whether the surgical event corresponds to the nociception event comprises determining, by the processing circuitry, whether the nociception parameter of the patient is greater than or equal to the nociception threshold while the surgical event flag is set.

Example 3. The method of Example 2, further comprising: outputting, by the processing circuitry for display at a display device, the nociception parameter of the patient over time and a value of the surgical event flag over time.

Example 4. The method of any of Examples 1-3, wherein the indication of the surgical event comprises an indication of an amount of force associated with the surgical event, the method further comprising: determining, by the processing circuitry, how much to adjust the amount of analgesic administered to the patient based at least in part on the amount of force associated with the surgical event.

Example 5. The method of any of Examples 1-4, wherein the indication of the surgical event comprises an indication of a physiological feature of the patient being incised by a robotic surgical system, the method further comprising: determining, by the processing circuitry, how much to adjust the amount of analgesic administered to the patient based at least in part on the physiological feature of the patient being incised by the robotic surgical system.

Example 6. The method of any of Examples 1-5, wherein providing the indication to adjust the amount of analgesic administered to the patient comprises: sending, by the processing circuitry to an analgesia administration device, the indication to adjust the amount of analgesic administered to the patient.

Example 7. The method of any of Examples 1-6, further comprising: in response to providing the indication to adjust the amount of analgesic administered to the patient, sending, by the processing circuitry to a robotic surgical system, an indication to restart making further incisions.

Example 8. The method of any of Examples 1-7, further comprising: determining, by the processing circuitry, whether to adjust the amount of analgesic administered to the patient based on a total amount of analgesic administered to the patient during surgery.

Example 9. The method of any of Examples 1-8, wherein comparing the nociception parameter of the patient to the nociception threshold comprises determining, by the processing circuitry, a sharp rise in the nociception parameter of the patient.

Example 10. A system comprising: memory configured to store a nociception threshold; and processing circuitry configured to: receive an indication of a surgical event; obtain a nociception parameter of a patient; compare the nociception parameter of the patient to the nociception threshold to detect a nociception event; determine whether the surgical event corresponds to the nociception event; and in response to determining whether the surgical event corresponds to the nociception event, provide an indication to adjust an amount of analgesic administered to the patient.

Example 11. The system of Example 10, wherein the processing circuitry is further configured to, in response to receiving the indication of the surgical event, set a surgical event flag; and wherein to determine whether the surgical event corresponds to the nociception event, the processing circuitry is further configured to determine whether the nociception parameter of the patient is greater than or equal to the nociception threshold while the surgical event flag is set.

Example 12. The system of Example 11, wherein the processing circuitry is further configured to output, for display at a display device, the nociception parameter of the patient over time and a value of the surgical event flag over time.

Example 13. The system of any of Examples 10-12, wherein the indication of the surgical event comprises an indication of an amount of force associated with the surgical event, and wherein the processing circuitry is further configured to: determine how much to adjust the amount of analgesic to administer to the patient based at least in part on the amount of force associated with the surgical event.

Example 14. The system of any of Examples 10-13, wherein the indication of the surgical event comprises an indication of a physiological feature of the patient being incised by a robotic surgical system, wherein the processing circuitry is further configured to: determine how much to adjust the amount of analgesic to administer to the patient based at least in part on the physiological feature of the patient being incised by the robotic surgical system.

Example 15. The system of any of Examples 10-14, wherein to provide the indication to adjust the amount of analgesic to administer to the patient, the processing circuitry is further configured to: send, to an analgesia administration device, the indication to adjust the amount of analgesic administered to the patient.

Example 16. The system of any of Examples 10-15, wherein the processing circuitry is further configured to: in response to providing the indication to adjust the amount of analgesic to administer to the patient, send, to a robotic surgical system, an indication to restart making further incisions.

Example 17. The system of any of Examples 10-16, wherein the processing circuitry is further configured to: determine whether to increase the amount of analgesic administered to the patient based on a total amount of analgesic administered to the patient during surgery.

Example 18. The system of any of Examples 10-17, wherein to compare the nociception parameter of the patient to the nociception threshold, the processing circuitry is further configured to determine a sharp rise in the nociception parameter of the patient.

Example 19. A non-transitory computer readable storage medium comprising instructions that, when executed, cause processing circuitry to: receive an indication of a surgical event; obtain a nociception parameter of a patient; compare the nociception parameter of the patient to a nociception threshold to detect a nociception event; determine whether the surgical event corresponds to the nociception event; and in response to determinizing whether the surgical event corresponds to the nociception event, provide an indication to adjust an amount of analgesic to administer to the patient.

Example 20. The non-transitory computer readable storage medium of Example 19, wherein the instructions further cause the processing circuitry to, in response to receiving, the indication of the surgical event, set a surgical event flag; and wherein to determine whether the surgical event corresponds to the nociception event, the instructions further cause the processing circuitry to determine whether the nociception parameter of the patient is greater than or equal to the nociception threshold while the surgical event flag is set.

The techniques described in this disclosure, including those attributed to patient monitoring system 2, processing circuitry 50, control circuitry 42, sensing circuitries 54, 56, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices. Processing circuitry, control circuitry, and sensing circuitry, as well as other processors and controllers described herein, may be implemented at least in part as, or include, one or more executable applications, application modules, libraries, classes, methods, objects, routines, subroutines, firmware, and/or embedded code, for example.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. The computer-readable medium may be an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

The functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements.

What is claimed is:

1. A method comprising:
   receiving, by processing circuitry, an indication of an occurrence of a surgical event during a period of time;
   setting, by the processing circuitry, a surgical event flag during the period of time based on receiving the indication of the occurrence of the surgical event;
   receiving, by the processing circuitry, a nociception parameter of a patient during the period of time;
   determining, by the processing circuitry, a nociception event based on comparing the nociception parameter of the patient to a nociception threshold; and
   providing, by the processing circuitry, an indication to adjust an amount of analgesic administered to the patient based on the surgical event corresponding to the nociception event during the period of time.

2. The method of claim 1, comprising
determining, by the processing circuitry, that the surgical event corresponds to the nociception event based on the nociception parameter of the patient being greater than or equal to the nociception threshold while the surgical event flag is set during the period of time.

3. The method of claim 2, comprising outputting, by the processing circuitry for display at a display device, the nociception parameter of the patient over time and a value of the surgical event flag over time.

4. The method of claim 1, wherein the indication of the occurrence of the surgical event comprises an indication of an amount of force associated with the surgical event, and wherein the method comprises determining, by the processing circuitry, an adjustment amount associated with the indication to adjust the amount of analgesic administered to the patient based at least in part on the amount of force associated with the surgical event.

5. The method of claim 1, wherein the indication of the occurrence of the surgical event comprises an indication of a physiological feature of the patient being incised by a robotic surgical system, and wherein the method comprises determining, by the processing circuitry, an adjustment amount associated with the indication to adjust the amount of analgesic administered to the patient based at least in part on the physiological feature of the patient being incised by the robotic surgical system.

6. The method of claim 1, comprising sending, by the processing circuitry to an analgesia administration device, the indication to adjust the amount of analgesic administered to the patient.

7. The method of claim 1, comprising, in response to providing the indication to adjust the amount of analgesic administered to the patient, sending, by the processing circuitry to a robotic surgical system, an indication to make an incision.

8. The method of claim 1, comprising determining, by the processing circuitry, to provide the indication to_adjust the amount of analgesic administered to the patient based on a total amount of analgesic administered to the patient during surgery.

9. The method of claim 1, comprising determining, by the processing circuitry, the nociception event based on an increase over time in the nociception parameter of the patient during the period of time.

10. A system comprising:
memory configured to store a nociception threshold; and
processing circuitry configured to:
receive an indication of an occurrence of a surgical event during a period of time;
set a surgical event flag during the period of time based on receiving the indication of the occurrence of the surgical event;
receive a nociception parameter of a patient during the period of time;
determine a nociception event based on comparing the nociception parameter of the patient to the nociception threshold; and
provide an indication to adjust an amount of analgesic administered to the patient based on determining that the surgical event corresponds to the nociception event during the period of time.

11. The system of claim 10,
wherein the processing circuitry is configured to determine that the surgical event corresponds to the nociception event based on the nociception parameter of the patient being greater than or equal to the nociception threshold while the surgical event flag is set during the period of time.

12. The system of claim 11, wherein the processing circuitry is configured to output, for display at a display device, the nociception parameter of the patient over time and a value of the surgical event flag over time.

13. The system of claim 10, wherein the indication of the occurrence of the surgical event comprises an indication of an amount of force associated with the surgical event, and wherein the processing circuitry is configured to determine an adjustment amount associated with the indication to adjust the amount of analgesic to administer to the patient based at least in part on the amount of force associated with the surgical event.

14. The system of claim 10, wherein the indication of the occurrence of the surgical event comprises an indication of a physiological feature of the patient being incised by a robotic surgical system, and wherein the processing circuitry is configured to determine an adjustment amount associated with the indication to adjust the amount of analgesic to administer to the patient based at least in part on the physiological feature of the patient being incised by the robotic surgical system.

15. The system of claim 10, wherein the processing circuitry is configured to send, to an analgesia administration device, the indication to adjust the amount of analgesic administered to the patient.

16. The system of claim 10, wherein the processing circuitry is configured to in response to providing the indication to adjust the amount of analgesic to administer to the patient, send, to a robotic surgical system, an indication to make an incision.

17. The system of claim 10, wherein the processing circuitry is configured to determine to provide the indication to increase the amount of analgesic administered to the patient based on a total amount of analgesic administered to the patient during surgery.

18. The system of claim 10, wherein the processing circuitry is configured to determine the nociception event based on an increase over time in the nociception parameter of the patient during the period of time.

19. A non-transitory computer readable storage medium comprising instructions that, when executed, cause processing circuitry to:
receive an indication of an occurrence of a surgical event during a period of time;
set a surgical event flag during the period of time based on receiving the indication of the occurrence of the surgical event;
receive a nociception parameter of a patient;
determine a nociception event based on comparing the nociception parameter of the patient to a nociception threshold; and
provide an indication to adjust an amount of analgesic to administer to the patient based on determining that the surgical event corresponds to the nociception event during the period of time.

20. The non-transitory computer readable storage medium of claim 19, wherein the instructions further cause the processing circuitry to determine that the surgical event corresponds to the nociception event, based on the nociception parameter of the patient being greater than or equal to the nociception threshold while the surgical event flag is set during the period of time.

* * * * *